United States Patent [19]

Los

[11] Patent Number: 5,021,078

[45] Date of Patent: Jun. 4, 1991

[54] 2-(2-IMIDAZOLIN-2-YL)PYRIDINES AND QUINOLINES, PROCESS AND INTERMEDIATES FOR THE PREPARATION THEREOF, AND USE OF SAID COMPOUNDS AS HERBICIDAL AGENTS

[75] Inventor: Marinus Los, Pennington, N.J.

[73] Assignee: American Cyanamid Company, Stamford, Conn.

[21] Appl. No.: 484,754

[22] Filed: Feb. 26, 1990

Related U.S. Application Data

[60] Division of Ser. No. 280,906, Dec. 9, 1988, Pat. No. 4,923,504, which is a division of Ser. No. 850,192, Apr. 10, 1986, Pat. No. 4,798,619, which is a division of Ser. No. 382,041, May 25, 1982, Pat. No. 4,638,068, which is a continuation-in-part of Ser. No. 252,704, Apr. 8, 1981, abandoned, which is a continuation-in-part of Ser. No. 155,909, Jun. 2, 1980, abandoned, Ser. No. 155,910, Jun. 2, 1980, abandoned, Ser. No. 155,867, Jun. 2, 1980, abandoned, Ser. No. 155,908, Jun. 2, 1980, abandoned, and Ser. No. 155,865, Jun. 2, 1980, abandoned.

[51] Int. Cl.$^5$ .................... A01N 43/90; C07D 471/04
[52] U.S. Cl. ............................................ 71/66; 71/94; 546/84; 546/113
[58] Field of Search ...................... 546/84, 113; 71/66, 71/94

[56] References Cited

U.S. PATENT DOCUMENTS 3,525,747  8/1970  Jacobs ................................. 546/113

*Primary Examiner*—Bernard I. Dentz
*Attorney, Agent, or Firm*—H. G. Jackson

[57] ABSTRACT

There are provided novel 2-(2-imidazolin-2-yl)pyridine and quinoline compounds, a process and intermediate compounds for the preparation thereof, and a method for controlling a wide variety of annual asnd perennial plant species therewith.

19 Claims, No Drawings

2-(2-IMIDAZOLIN-2-YL)PYRIDINES AND QUINOLINES, PROCESS AND INTERMEDIATES FOR THE PREPARATION THEREOF, AND USE OF SAID COMPOUNDS AS HERBICIDAL AGENTS

This is a divisional application of Ser. No. 07/280,906 filed Dec. 9, 1988, now U.S. Pat. No. 4,923,504 which is a divisional of Ser. No. 850,192 filed Apr. 10, 1986 which is now U.S. Pat. No. 4,798,619 (1989), which is a division of Ser. No. 382,041 filed May 25, 1982 which is now U.S. Pat. No. 4,638,068 (1987), which is a continuation-in-part of Ser. No. 252,704 filed Apr. 8, 1981, now abandoned, which is a continuation-in-part of abandoned applications Ser. Nos. 155,909, 155,910, 155,867, 155,908 and 155,865 all filed Jun. 2, 1980.

SUMMARY OF THE INVENTION

The invention is intermediates and herbicidal compounds of the formulas:

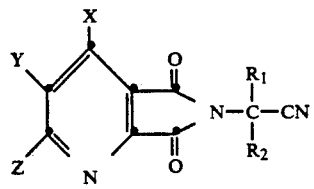

or

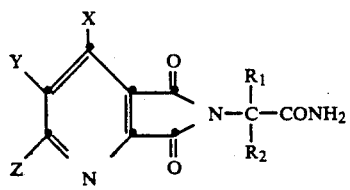

wherein $R_1$ is $C_1-C_4$ alkyl;

$R_2$ is $C_1-C_4$ alkyl or $C_3-C_6$ cycloalkyl; and when $R_1$ and $R_2$ are taken together with the carbon to which they are attached they may represent $C_3-C_6$ cycloalkyl optionally substituted with methyl;

X is hydrogen, halogen, hydroxyl or methyl, with the proviso that when Y and Z are taken together to form a ring and YZ is represented by the structure: $-(CH_2)_n-$, where n is 3 or 4, X is hydrogen;

Y and Z are each hydrogen, halogen, $C_1-C_6$ alkyl, hydroxyloweralkyl, $C_1-C_6$ alkoxy, $C_1-C_4$ alkylthio, phenoxy, $C_1-C_4$ haloalkyl, nitro, cyano, $C_1-C_4$ alkylamino, diloweralkylamino or $C_1-C_4$ alkylsulfonyl group, or phenyl optionally substituted with one $C_1-C_4$ alkyl, $C_1-C_4$ alkoxy or halogen; and, when taken together, Y and Z may form a ring in which YZ are represented by the structure: $-(CH_2)_n-$, where n is an integer of 3 or 4, provided that X is hydrogen; or

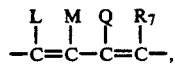

where L, M, Q and $R_7$ are each hydrogen, halogen, $C_1-C_4$ alkyl, $C_1-C_4$ alkoxy, $C_1-C_4$ alkylthio, $C_1-C_4$ alkylsulfonyl, $C_1-C_4$ haloalkyl, $NO_2$, CN, phenyl, phenoxy, amino, $C_1-C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$ may represent a substituent other than hydrogen, halogen, $C_1-C_4$ alkyl or $C_1-C_4$ alkoxy.

INCORPORATION BY REFERENCE

The specification of U.S. Pat. No. 4,638,068 (1987) which was parent application U.S. Ser. No. 382,041, filed May 5, 1982 is hereby incorporated by reference.

I claim:

1. A compound having the structure:

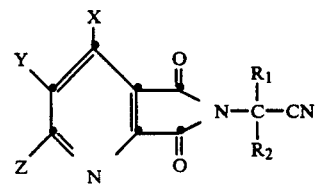

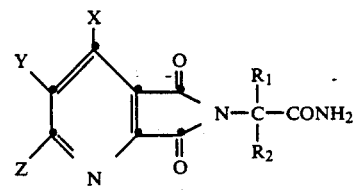

wherein $R_1$ is $C_1-C_4$ alkyl;

$R_2$ is $C_1-C_4$ alkyl or $C_3-C_6$ cycloalkyl; and when $R_1$ and $R_2$ are taken together with the carbon to which they are attached they may represent $C_3-C_6$ cycloalkyl optionally substituted with methyl;

X is hydrogen, halogen, hydroxyl or methyl, with the proviso that when Y and Z are taken together to form a ring and YZ is represented by the structure: $-(CH_2)_n-$, where n is 3 or 4, X is hydrogen;

Y and Z are each hydrogen, halogen, $C_1-C_6$ alkyl, hydroxyloweralkyl, $C_1-C_6$ alkoxy, $C_1-C_4$ alkylthio, phenoxy, $C_1-C_4$ haloalkyl, nitro, cyano, $C_1-C_4$ alkylamino, diloweralkylamino or $C_1-C_4$ alkylsulfonyl group, or phenyl optionally substituted with one $C_1-C_4$ alkyl, $C_1-C_4$ alkoxy or halogen; and, when taken together, Y and Z may form a ring in which YZ are represented by the structure: $-(CH_2)_n-$, where n is an integer of 3 or 4, provided that X is hydrogen; or

where L, M, Q and $R_7$ are each hydrogen, halogen, $C_1-C_4$ alkyl, $C_1-C_4$ alkoxy, $C_1-C_4$ alkylthio, $C_1-C_4$ alkylsulfonyl, $C_1-C_4$ haloalkyl, $NO_2$, CN, phenyl, phenoxy, amino, $C_1-C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$ may represent a substituent other than hydrogen, halogen, $C_1-C_4$ alkyl or $C_1-C_4$ alkoxy.

2. A compound according to claim 1 having the structure:

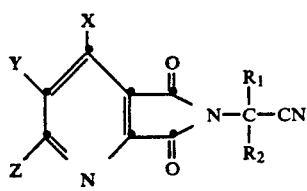

wherein $R_1$, $R_2$, X, Y and Z are as described therein.

3. A compound according to claim 1 having the structure:

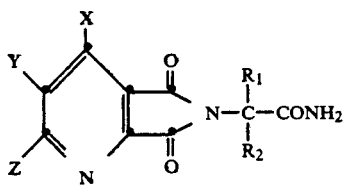

wherein $R_1$, $R_2$, X, Y and Z are as described therein.

4. A compound according to claim 2, 5,7-dihydro-α-isopropyl-α-methyl-5,7-dioxo-6H-pyrrolo[3,4-b]pyridine-6-acetonitrile.

5. A compound according to claim 2, α-cyclopropyl-5,7-dihydro-α-methyl-5,7-dioxo-6H-pyrrolo[3,4-b]pyridine-6-acetonitrile.

6. A compound according to claim 2, 5,7-dihydro-α-isopropyl-2-methoxy-α-methyl-5,7-dioxo-6H-pyrrolo[3,4-b]pyridine-6-acetonitrile.

7. A compound according to claim 2, 1,3-dihydro-α-isopropyl-α-methyl-1,3-dioxo-2H-pyrrolo[3,4-b]quinoline-2-acetonitrile.

8. A compound according to claim 2, 2-chloro-5,7-dihydro-α-isopropyl-α-methyl-5,7-dioxo-6H-pyrrolo[3,4-b]pyridine-6-acetonitrile.

9. A compound according to claim 3, 1,3-dihydro-α-isopropyl-α-methyl-1,3-dioxo-2H-pyrrolo[3,4-b]quinoline-2-acetamide.

10. A compound according to claim 3, 2-chloro-5,7-dihydro-α-isopropyl-α-methyl-5,7-dioxo-6H-pyrrolo[3,4-b]pyridine-6-acetamide.

11. A compound according to claim 3, 5,7-dihydro-α-isopropyl-2-methoxy-α-methyl-5,7-dioxo-6H-pyrrolo[3,4-b]pyridine-6-acetamide.

12. A compound according to claim 3, 3-bromo-5,7-dihydro-α-isopropyl-α-methyl-5,7-dioxo-6H-pyrrolo[3,4-b]pyridine-6-acetamide.

13. A compound according to claim 3, 5,7-dihydro-α-isopropyl-α-methyl-5,7-dioxo-6H-pyrrolo[3,4-b]pyridine-6-acetamide.

14. A method for the control of monocotyledonous and dicotyledonous annual, perennial and aquatic plant species comprising: applying to the foliage of said plants or to soil or water containing seeds or other propogating organs thereof, a herbicidally effective amount of a compound having a structure:

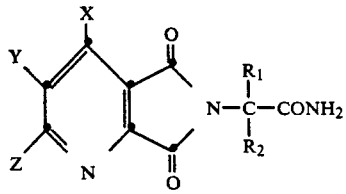

wherein
$R_1$ is $C_1$-$C_4$ alkyl;
$R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl;
X is hydrogen, halogen, hydroxyl or methyl, with the proviso that when Y and Z are taken together to form a ring and YZ is represented by the structure: —$(CH_2)_n$—, where n is 3 or 4, X is hydrogen;
Y and Z are each hydrogen, halogen, $C_1$-$C_6$ alkyl, hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino or $C_1$-$C_4$ alkylsulfonyl group, or phenyl optionally substituted with one $C_1$-$C_4$ alkyl, $C_1$-$C_4$ alkoxy or halogen; and, when taken together, Y and Z may form a ring in which YZ are represented by the structure: —$(CH_2)_n$—, where n is an integer of 3 or 4, provided that X is hydrogen; or

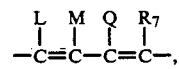

where L, M, Q and $R_7$ are each hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $C_1$-$C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$ may represent a substituent other than hydrogen, halogen, $C_1$-$C_4$ alkyl or $C_1$-$C_4$ alkoxy.

15. A method according to claim 14, wherein said compound is applied to the foliage of said plants or to soil or water containing seeds or other propagating organs of said plants at a rate between about 0.16 to 4.0 kg/ha.

16. A herbicidal composition comprising an inert solid or liquid diluent and a herbicidally effective amount of a compound having a structure:

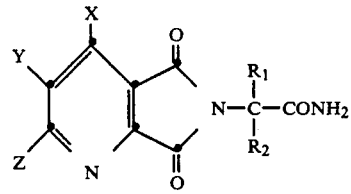

wherein
$R_1$ is $C_1$-$C_4$ alkyl;
$R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl;
X is hydrogen, halogen, hydroxyl or methyl, with the proviso that when Y and Z are taken together to form a ring and YZ is represented by the structure: —$(CH_2)_n$—, where n is 3 or 4, X is hydrogen;
Y and Z are each hydrogen, halogen, $C_1$-$C_6$ alkyl, hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino or $C_1$-$C_4$ alkylsulfonyl group, or phenyl optionally substituted with one $C_1$-$C_4$ alkyl, $C_1$-$C_4$ alkoxy or halogen; and, when taken together, Y and Z may form a ring in which YZ are represented by the structure: —(CH$_2$)$_n$—, where n is an integer of 3 or 4, provided that X is hydrogen; or

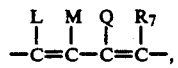

where L, M, Q and R$_7$ are each hydrogen, halogen, C$_1$-C$_4$ alkyl, C$_1$-C$_4$ alkoxy, C$_1$-C$_4$ alkylthio, C$_1$-C$_4$ alkylsulfonyl, C$_1$-C$_4$ haloalkyl, NO$_2$, CN, phenyl, phenoxy, amino, C$_1$-C$_4$ alkylamino, diloweralkylamino, chlorophenyl, methylphenyl, or phenoxy substituted with one Cl, CF$_3$, NO$_2$ or CH$_3$ group, with the proviso that only one of L, M, Q or R$_7$ may represent a substituent other than hydrogen, halogen, C$_1$-C$_4$ alkyl or C$_1$-C$_4$ alkoxy.

17. A solid herbicidal composition according to claim 16, comprising from 20% to 45% by weight of a finely divided solid inert carrier; from 45% to 80% by weight of the herbicidally effective ingredient represented by structures a, b, c, d or e; from about 2% to 5% by weight of a dispersing agent and from about 2% to 5% by weight of a surface active agent.

18. A liquid herbicidal composition according to claim 16, comprising from 5% to 25% by weight of the herbicidally effective ingredient represented by structures a, b, c, d or e; from about 65% to 90% by weight of an inert organic solvent and from about 5% to 10% by weight of a surface active agent.

19. A granular herbicidal composition according to claim 16, comprising from about 80% to 97% by weight of an inert granular carrier and from about 3% to 20% by weight of the herbicidally effective ingredient represented by structures a, b, c, d or e.

* * * * *